(12) United States Patent
Shim

(10) Patent No.: US 11,553,836 B2
(45) Date of Patent: Jan. 17, 2023

(54) PERORAL ENDOSCOPIC APPARATUS

(71) Applicant: ENDOLFIN CO., LTD., Anyang-si (KR)

(72) Inventor: Han Bo Shim, Seongnam-si (KR)

(73) Assignee: ENDOLFIN CO., LTD., Anyang-si (KR)

(*) Notice: Subject to any disclaimer, the term of this patent is extended or adjusted under 35 U.S.C. 154(b) by 1045 days.

(21) Appl. No.: 16/094,195

(22) PCT Filed: Aug. 31, 2018

(86) PCT No.: PCT/KR2018/010111
§ 371 (c)(1),
(2) Date: Oct. 16, 2018

(87) PCT Pub. No.: WO2019/050218
PCT Pub. Date: Mar. 14, 2019

(65) Prior Publication Data
US 2021/0219828 A1    Jul. 22, 2021

(30) Foreign Application Priority Data

Sep. 5, 2017 (KR) .......................... 10-2017-0113136

(51) Int. Cl.
*A61B 1/04*       (2006.01)
*A61B 1/00*       (2006.01)
(Continued)

(52) U.S. Cl.
CPC .......... *A61B 1/041* (2013.01); *A61B 1/00006* (2013.01); *A61B 1/00009* (2013.01);
(Continued)

(58) Field of Classification Search
CPC ............ A61B 1/00006; A61B 1/00009; A61B 1/00016; A61B 1/00025; A61B 1/00034;
(Continued)

(56) References Cited

U.S. PATENT DOCUMENTS

| | | | |
|---|---|---|---|
| 4,327,738 A * | 5/1982 | Green | A61B 1/042 348/65 |
| 11,006,975 B1 * | 5/2021 | Cohen | A61B 17/3421 |
| 2003/0060734 A1 * | 3/2003 | Yokoi | A61B 1/00158 600/593 |

(Continued)

FOREIGN PATENT DOCUMENTS

| | | |
|---|---|---|
| CN | 201641948 U | 11/2010 |
| JP | H0542155 A | 2/1993 |

(Continued)

OTHER PUBLICATIONS

The extended European search report of EP 18854146, dated Apr. 6, 2021.

*Primary Examiner* — Baisakhi Roy
(74) *Attorney, Agent, or Firm* — STIP Law Group, LLC

(57) ABSTRACT

Disclosed is a peroral endoscopic apparatus of a swallowable type, the peroral endoscopic apparatus including: at least one imaging unit configured to perform imaging of a human body digestive system and output image data; at least one ultrasonic unit configured to output ultrasonic data on a submucosal region of the digestive system and a peripheral organ located therearound; a magnetic unit configured to adjust a position, a posture, and a proceeding direction of the peroral endoscopic apparatus in response to an external magnetic force; a transceiving unit configured to transmit the image data and the ultrasonic data to an external device or receive an external control signal; a control unit configured to control the imaging unit and the ultrasonic unit to perform imaging of the digestive system and the submucosal region simultaneously or individually; and a power supply unit configured to supply power.

12 Claims, 10 Drawing Sheets

(51) Int. Cl.
*A61B 1/05* (2006.01)
*A61B 8/12* (2006.01)
*A61B 8/00* (2006.01)

(52) U.S. Cl.
CPC ...... *A61B 1/00034* (2013.01); *A61B 1/00158* (2013.01); *A61B 1/05* (2013.01); *A61B 8/12* (2013.01); *A61B 8/4494* (2013.01)

(58) Field of Classification Search
CPC ....... A61B 1/041; A61B 8/12; A61B 1/00156; A61B 1/00158; A61B 8/445
See application file for complete search history.

(56) References Cited

U.S. PATENT DOCUMENTS

| | | | |
|---|---|---|---|
| 2003/0181788 A1 | 9/2003 | Yokoi et al. | |
| 2004/0092892 A1* | 5/2004 | Kagan | A61F 5/0079 604/264 |
| 2004/0133095 A1* | 7/2004 | Dunki-Jacobs | A61B 1/041 600/407 |
| 2007/0073105 A1* | 3/2007 | Honda | A61B 1/041 600/179 |
| 2007/0265496 A1 | 11/2007 | Kawano et al. | |
| 2008/0238259 A1* | 10/2008 | Osawa | H01L 41/293 310/334 |
| 2008/0281189 A1* | 11/2008 | Komuro | A61B 8/445 600/424 |
| 2012/0101386 A1* | 4/2012 | Arneson | A61B 8/12 600/447 |
| 2013/0324914 A1* | 12/2013 | Valdastri | A61M 13/003 604/26 |
| 2017/0311784 A1* | 11/2017 | Jang | A61B 1/0684 |
| 2017/0325688 A1* | 11/2017 | Gregersen | A61B 5/0062 |
| 2019/0015070 A1* | 1/2019 | Memon | A61B 10/0045 |

FOREIGN PATENT DOCUMENTS

| | | |
|---|---|---|
| JP | 2001269343 A | 10/2001 |
| JP | 2004350705 A | 12/2004 |
| JP | 2006129946 A | 5/2006 |
| JP | 2007195961 A | 8/2007 |
| KR | 1020100049336 A | 5/2010 |

* cited by examiner

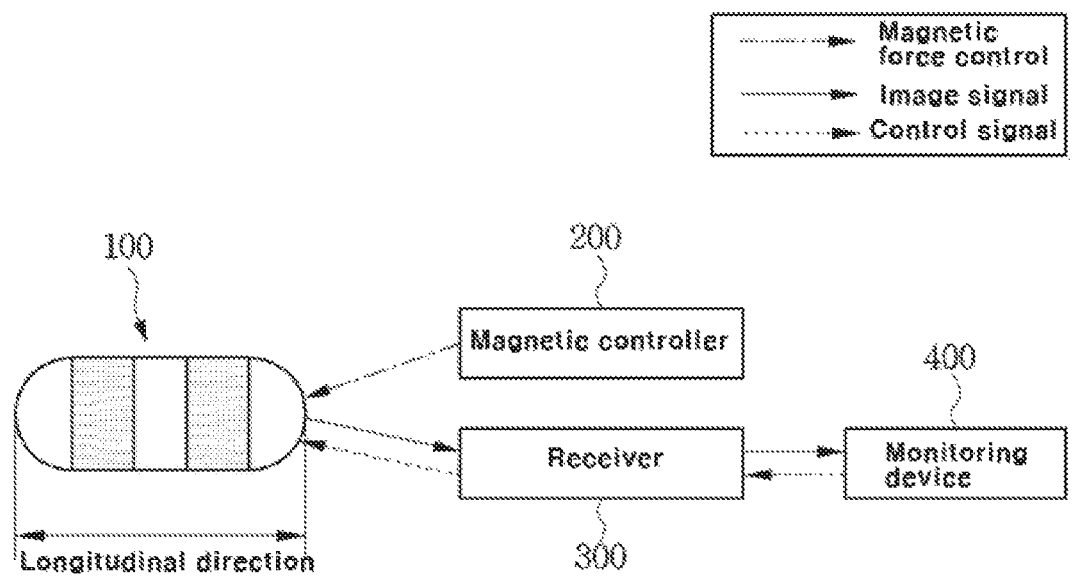
[FIG. 1]
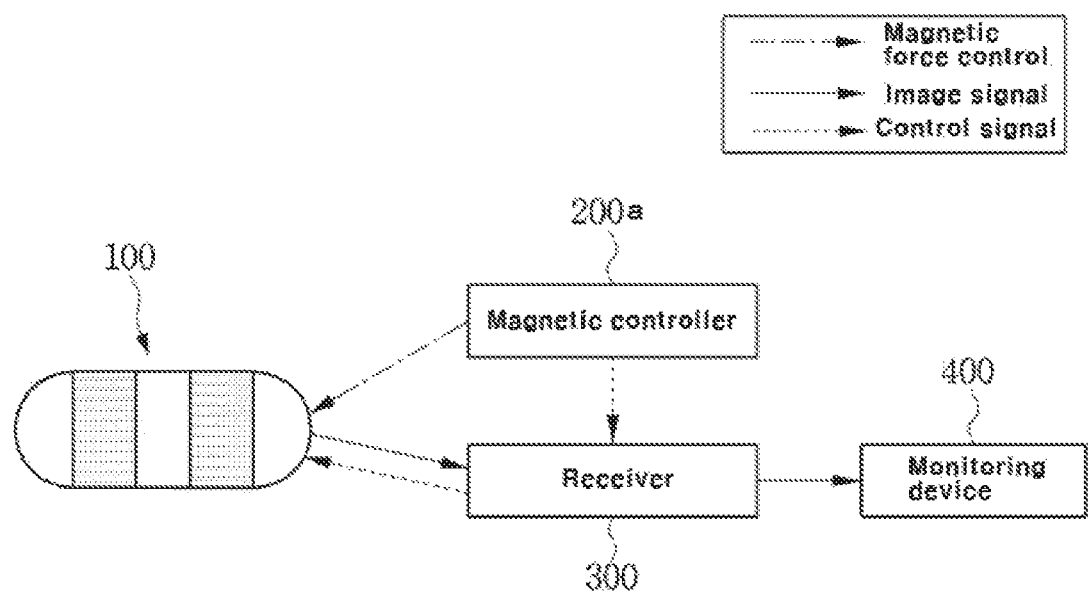
[FIG. 2]

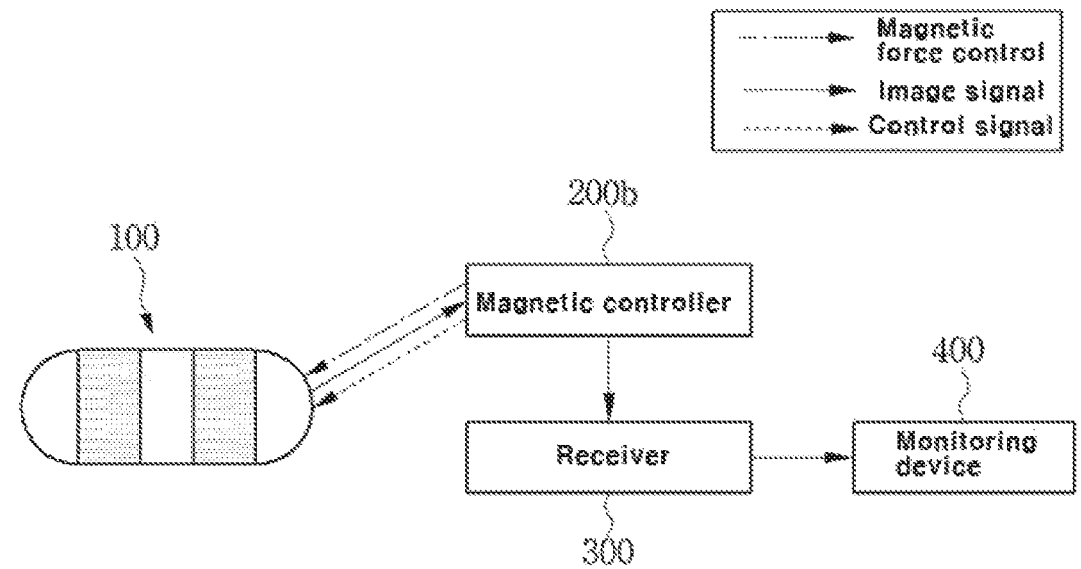
[FIG. 3]
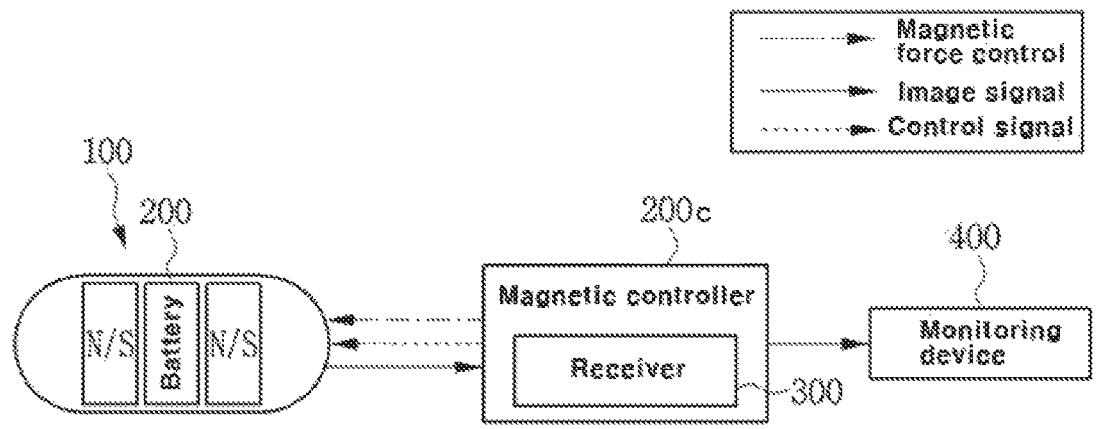
[FIG. 4]

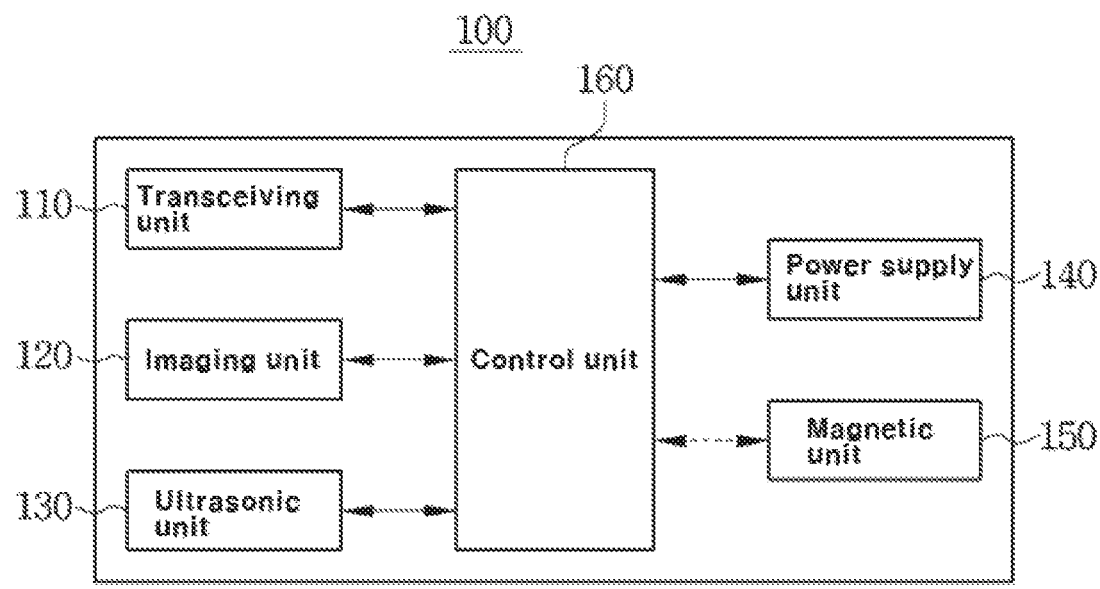
[FIG. 5]
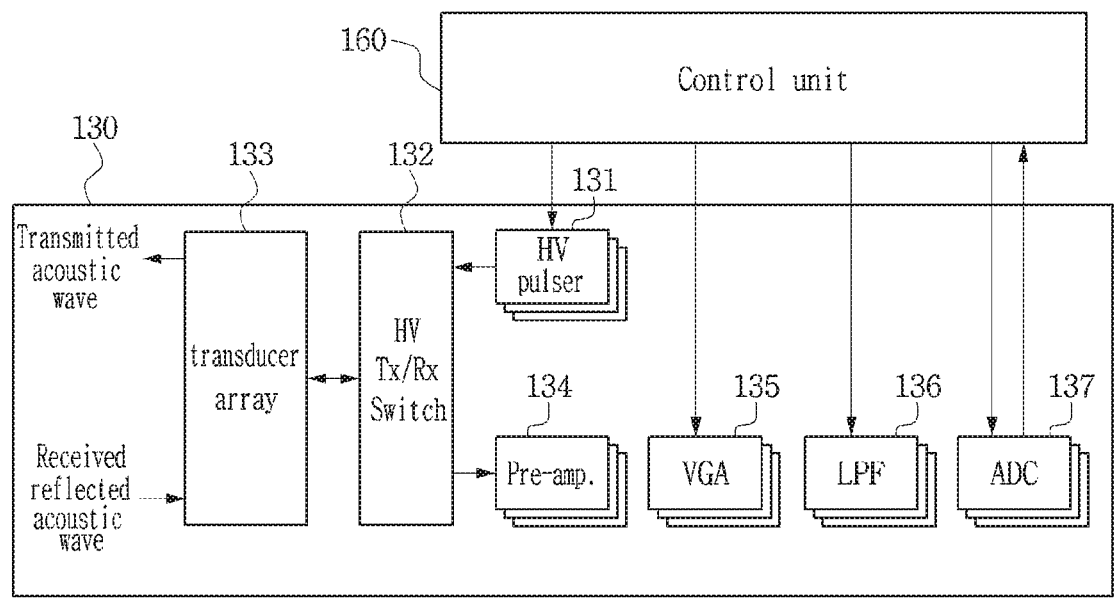
[FIG. 6]

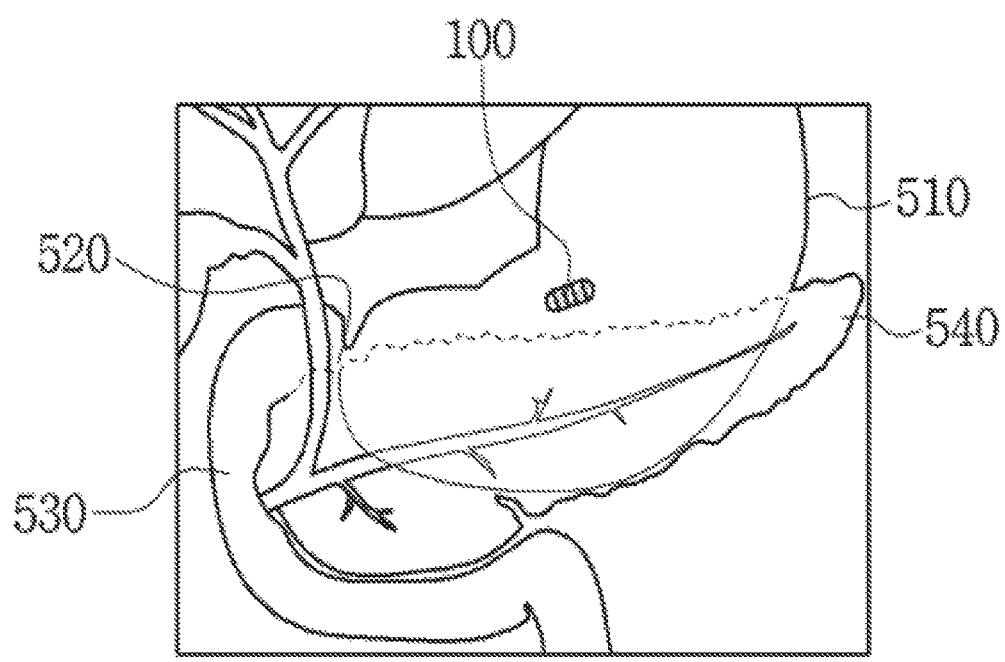
[FIG. 7]

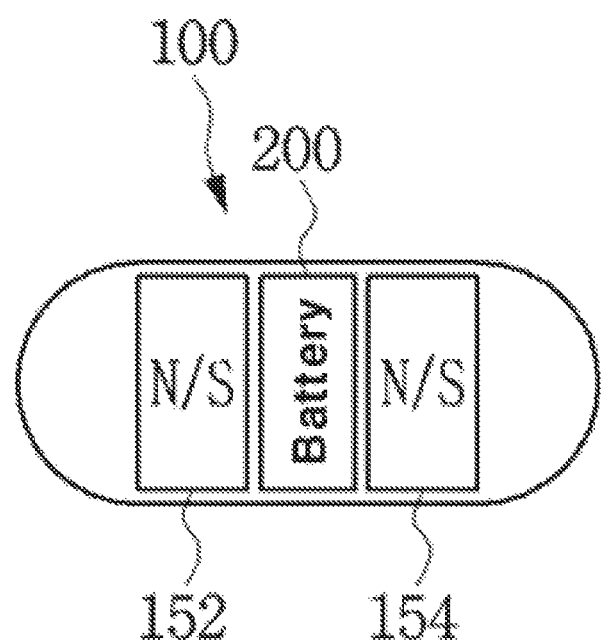
[FIG. 8]

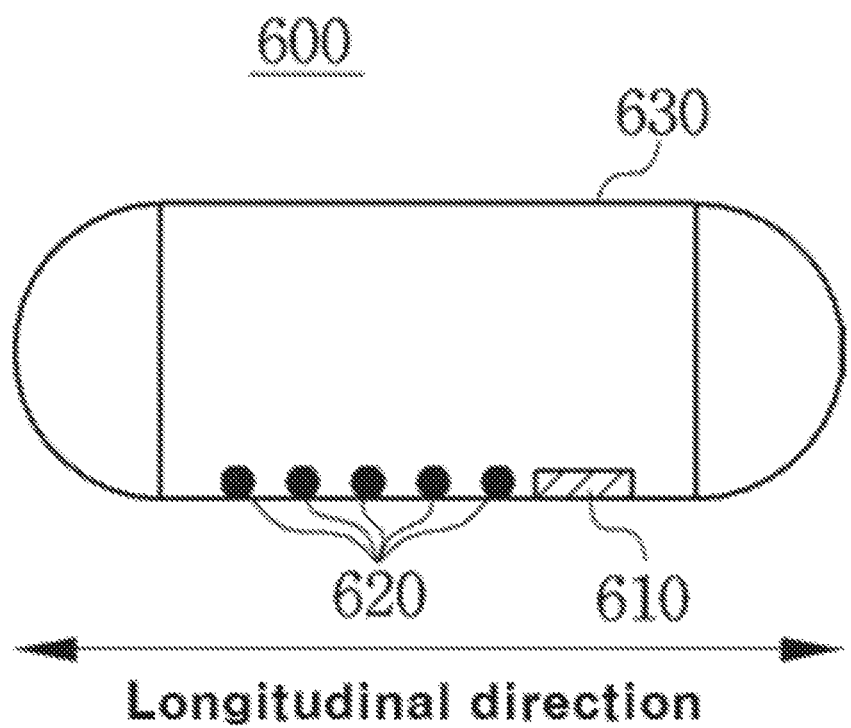
[FIG. 9]

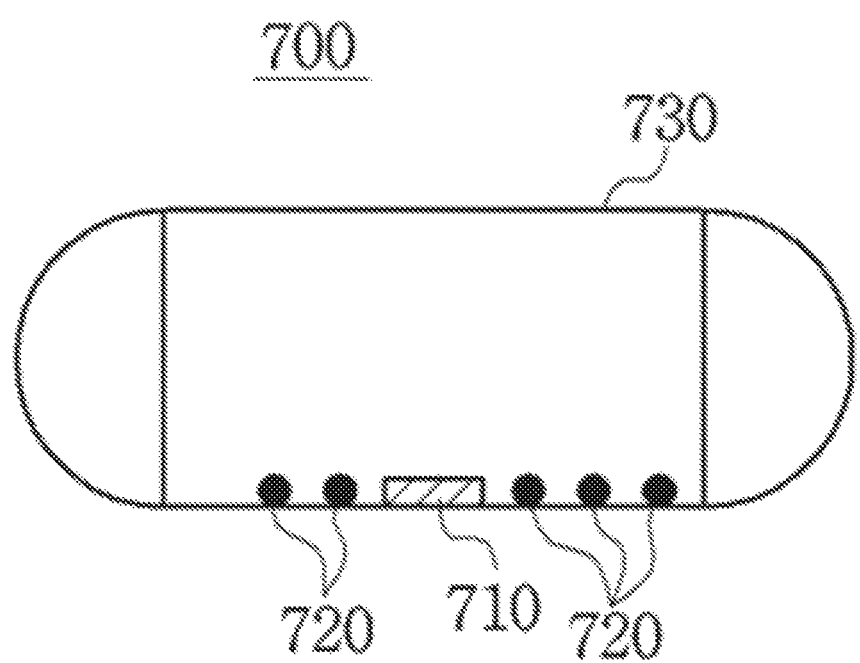
[FIG. 10]

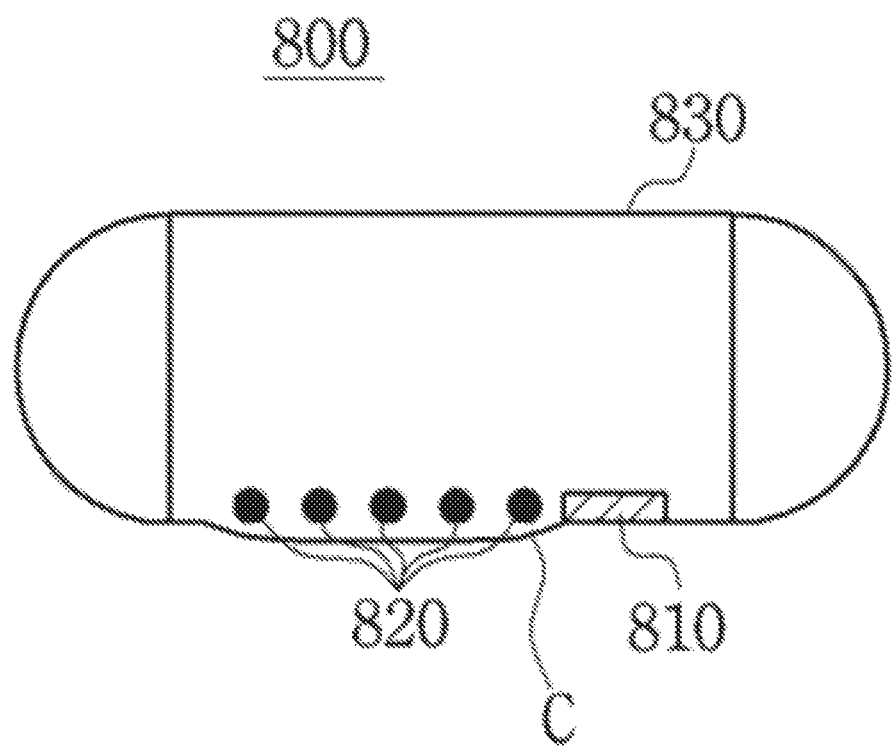
[FIG. 11]

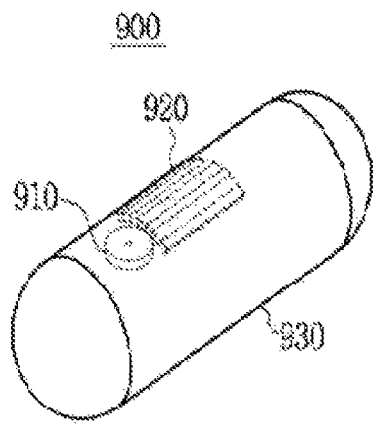
[FIG. 12A]
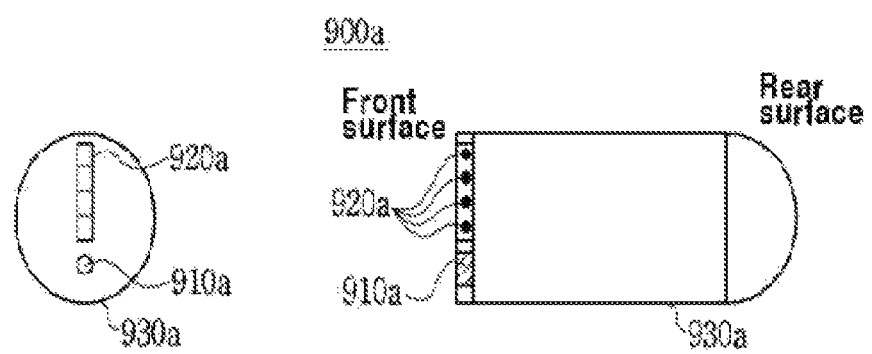
[FIG. 12B]

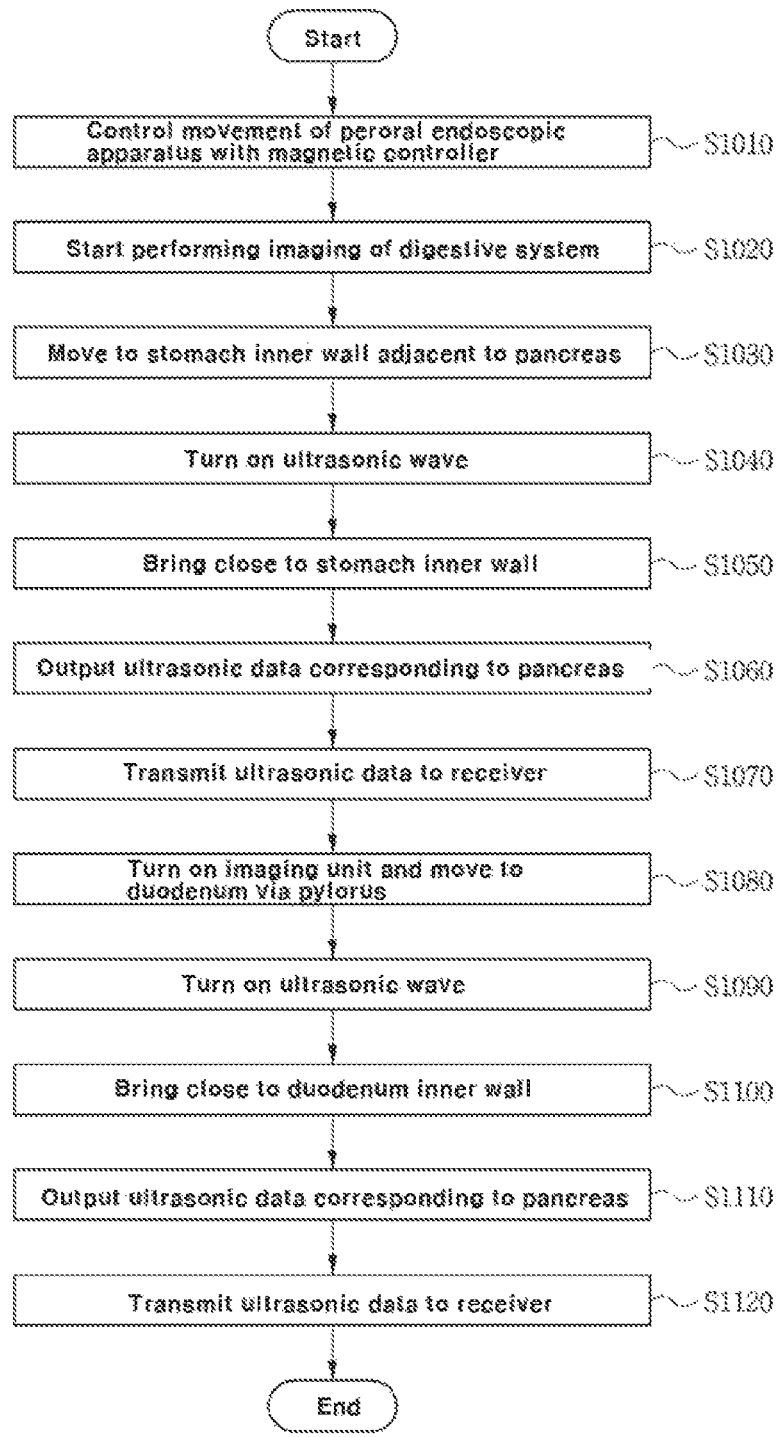
[FIG. 13]

PERORAL ENDOSCOPIC APPARATUS

CROSS-REFERENCE TO RELATED APPLICATIONS

This application is the U.S. National Phase under 35 U.S.C. § 371 of International Application No. PCT/KR2018/010111 filed on Aug. 31, 2018, which in turn claims the benefit of Korean Application No. 10-2017-0113136, filed on Sep. 5, 2017, the disclosures of which are incorporated by reference into the present application.

TECHNICAL FIELD

The present invention relates generally to a peroral endoscopic apparatus. More particularly, the present invention relates to a peroral endoscopic apparatus capable of monitoring the digestive system and peripheral organs around the digestive system.

BACKGROUND ART

The human digestive system is divided into the esophagus, stomach, small intestine, and large intestine. Normally, the esophagus and stomach are observed with an upper gastrointestinal endoscope that can be inserted into the distal part of the duodenum, and the large intestine is observed with a colonoscope capable of observing the end of the ileum, which is the distal end of the intestine.

However, in the case of the small intestine, an endoscope having established diagnostic and therapeutic methods has not yet been established. Therefore, various radiation diagnostic methods including small intestine barium angiography and CT have been applied to the small intestine, but the diagnosis rate for small intestinal diseases is relatively low.

In recent years, in order to solve such a problem, research and development of a peroral endoscope have been actively conducted. The peroral endoscope is a swallowable capsule endoscope that allows a close-up view of the esophagus, stomach, small intestine as well as the large intestine by small-sized camera.

However, a conventional peroral endoscope is problematic in that it is difficult to judge abnormal symptoms in the digestive system, to stop at a site where precise observation is required, or to move back to a site having been passed to observe again. This is because the conventional peroral endoscope moves passively by the peristaltic motion of the digestive tract, not by self-power.

In addition, some peroral endoscope systems control the position and posture of a peroral endoscope in the stomach from the outside using a magnetic device that forms a strong magnetic field around the human body. However, since the device for control is large, the required facility size must be large, and there is a disadvantage that the operation cost as well as the facility cost is high.

Further, studies have been attempted to detect submucosal and muscular tumors of the gastrointestinal tract and even peripheral organs around stomach such as the pancreas by applying an ultrasonic sensor to the conventional peroral endoscope, but the presence of an air layer between the peroral endoscope and the inner wall of the digestive tract makes it impossible to directly perform ultrasonic imaging. To solve this problem, bringing the peroral endoscope into close contact with the inner wall of the digestive system is employed as a solution, but problems remain. Therefore, in order to examine peripheral organs around the stomach, such as the pancreas, examination accompanied with the inconvenience of using a CT scan or an ultrasonic endoscope using a probe separately.

DISCLOSURE

Technical Problem

Accordingly, the present invention has been made keeping in mind the above problems occurring in the prior art, and an object of the present invention is to provide a peroral endoscopic apparatus, in which it is possible to control the posture, direction of movement, speed of movement, and direction of imaging, such that more accurate observation and diagnosis of each digestive organ including the stomach as well as the small intestine and large intestine are performed.

Another object of the present invention is to provide a peroral endoscopic apparatus, in which it is possible to more accurately diagnose a disease that is difficult to diagnose accurately only by using an endoscope, by using an ultrasonic method.

A further object of the present invention is to provide a peroral endoscopic apparatus, in which it is possible to examine the internal and external walls of the digestive system in detail while controlling the movement and imaging direction of the endoscopic apparatus, with small-sized and low cost equipment.

Still another object of the present invention is to provide a peroral endoscopic apparatus, in which it is possible to perform ultrasonic imaging of peripheral organs around the stomach without using an ultrasonic endoscope that uses a conventional probe.

These objects together with others not specifically mentioned will become clear to those skilled in the art from the following description.

Technical Solution

In order to accomplish the above object, the present invention provides a peroral endoscopic apparatus of a swallowable type, the peroral endoscopic apparatus including: at least one imaging unit configured to perform imaging of a human body digestive system while moving in the digestive system and output image data; at least one ultrasonic unit configured to output ultrasonic data on a region beneath an inner wall of the digestive system (hereinafter, referred to as 'submucosal region') and a peripheral organ located around the digestive system; a magnetic unit configured to adjust a position, a posture, and a proceeding direction of the peroral endoscopic apparatus in response to an external magnetic force; a transceiving unit configured to transmit the image data and the ultrasonic data to an external device or receive an external control signal; a control unit configured to control the at least one imaging unit and the at least one ultrasonic unit to perform imaging of the digestive system and the submucosal region simultaneously or individually; and a power supply unit configured to supply power to the at least one imaging unit, the at least one ultrasonic unit, the magnetic unit, the transceiving unit, and the control unit.

The external magnetic force may be generated by an external magnetic controller to drive the magnetic unit, and the magnetic controller may be configured to be brought close contact with or close to a patient's upper body to allow the external magnetic force to act on the magnetic unit.

The magnetic controller may control the magnetic unit such that the peroral endoscopic apparatus is moved to a stomach inner wall closest to the peripheral organ; and the control unit may control the at least one imaging unit to perform imaging of the closest stomach inner wall when the peroral endoscopic apparatus is moved to the stomach inner wall closest to the peripheral organ, and control the at least one ultrasonic unit to perform imaging of a submucosal region of the closest stomach.

For example, when the peripheral organ is a pancreas, the control unit may control the at least one ultrasonic unit to perform imaging of the pancreas by differentiating a frequency of performing imaging of a central part of the pancreas and a frequency of performing imaging of head and tail parts of the pancreas.

An image sensor of the at least one imaging unit and at least one ultrasonic transducer of the at least one ultrasonic unit may be arranged in parallel with each other along a same line of the peroral endoscopic apparatus to perform imaging toward a same direction in the digestive system.

When the ultrasonic transducer is provided in plural, the image sensor of the at least one imaging unit may be provided between the ultrasonic transducers such that an angle of view of the image sensor and an ultrasonic scanning range of the ultrasonic transducers are overlapped with each other.

Of the peroral endoscopic apparatus, a surface facing the at least one ultrasonic transducer may be formed as a curved surface having a positive curvature.

An image sensor of the at least one imaging unit and at least one ultrasonic transducer of the at least one ultrasonic unit may be arranged in two rows in parallel with each other along a circumference of the peroral endoscopic apparatus to perform imaging toward a same direction in the digestive system.

The at least one ultrasonic transducer of the at least one ultrasonic unit may be arranged along at least one arc that is a part of the circumference of the peroral endoscopic apparatus.

The magnetic unit may allow the peroral endoscopic apparatus to be brought in close contact with the inner wall of the digestive system by interaction with the external magnetic force.

The power supply unit may include at least one of a rechargeable battery and a regular battery other than the rechargeable battery.

The at least one ultrasonic unit may be provided to be in close contact with a surface of the peroral endoscopic apparatus facing the at least one ultrasonic unit; and of the peroral endoscopic apparatus, the surface facing the at least one ultrasonic unit may be formed to be flat.

The magnetic unit may include: a first permanent magnet and a second permanent magnet, wherein the power supply unit as a conductor is provided between the first permanent magnet and the second permanent magnet.

Advantageous Effects

According to the present invention, by using magnetic force, it is possible to control the posture, direction of movement, speed of movement, and direction of imaging, such that more accurate observation and diagnosis of each digestive organ including the stomach as well as the small intestine and large intestine are performed.

Further, according to the present invention, by using a small-sized ultrasonic element, it is possible to more accurately diagnose a disease that is difficult to diagnose accurately only by using a conventional optical peroral endoscope.

Further, according to the present invention, by having both magnetic and ultrasonic elements simultaneously, it is possible to examine the submucosal region as well as the inner wall of the digestive system in detail, with small-sized and low cost equipment.

Further, according to the present invention, by bringing the peroral endoscopic apparatus into close contact with the stomach inner wall using magnetic force, it is possible to perform ultrasonic imaging of the submucosal region of the stomach and peripheral organs around the stomach more clearly, and thus, a separate CT scan or an ultrasonic endoscope using a probe is not required, thereby improving convenience to a patient.

The effects of the present invention are not limited to those described above, and other effects not mentioned may be clearly understood by those skilled in the art from the following description.

DESCRIPTION OF DRAWINGS

FIGS. 1, 2, 3 and 4 are schematic views showing a peroral endoscope system with a peroral endoscopic apparatus of a swallowable type according to first to fourth embodiments of the present invention respectively applied thereto;

FIG. 5 is a block diagram showing the peroral endoscopic apparatus according to the embodiment of the present invention;

FIG. 6 is a block diagram showing an ultrasonic unit according to the embodiment of the present invention;

FIG. 7 is a view showing the stomach and the pancreas located around the stomach of the human digestive system;

FIG. 8 is a conceptual view showing an example of arrangement of two permanent magnets and a power supply unit;

FIGS. 9, 10, 11, 12A, and 12B are conceptual views showing first to fifth peroral endoscopic apparatuses according to first to fifth embodiments of the present invention; and FIG. 13 is a flow chart showing how to perform endoscopy of the pancreas with the peroral endoscopic apparatus according to the embodiment of the present invention.

MODE FOR INVENTION

The above and other related objects and features of the invention will be readily understood by the following preferred embodiments with reference to the accompanying drawings. However, the present invention is not limited to the embodiments described herein but may be embodied in other forms. Rather, the embodiments disclosed herein are provided so that the disclosure can be thorough and complete, and will fully convey the idea of the present invention to those skilled in the art.

When one portion is referred to as being "on" other portion, it may be directly on the other portion or may be involved with another portion in between. In contrast, when one portion is referred to as being "directly on" other portion, no other portion is involved in between. Further, in the drawings, the thickness of the components is exaggerated for an effective description of the technical content.

The terms such as first, second, third, etc. are used to describe various parts, components, regions, layers and/or sections, but are not limited thereto. These terms are only used to distinguish one element from another. The embodiments described and exemplified herein also include their complementary embodiments.

It will be further understood that when the first element is said to be operated or executed on the second element, the first element is either operated executed in the environment in which the second element is operated or executed, or operated or executed through direct or indirect interaction with the second element.

When it is mentioned that an element, component, apparatus, or system includes a component constituted by a program or software, it is to be understood that the element, component, device, or system. includes hardware (e.g., a memory, CPU, etc) required for implementing or operating the program or software or other programs or software (e.g., a driver needed to drive an operating system or hardware) even without explicit mention.

It should be further understood that unless otherwise specified in the implementation of an element, the element may be implemented in software, hardware, or any form of software and hardware.

Further, the terminology used herein is for the purpose of describing particular embodiments only and is not intended to be limiting of the present invention. As used herein, the singular forms are intended to include the plural forms as well, unless the context clearly indicates otherwise. The terms "comprises" and/or "comprising" used in the specification do not exclude the presence or addition of at least one other element.

Hereinbelow, the present invention will be described in detail with reference to the accompanying drawings. In describing the specific embodiments below, various specific details are set forth to further illustrate and assist in understanding the present invention. However, those skilled in the art can understand that the present invention can be used without any of these specific details.

In the following description, it is to be noted that, when the functions of conventional elements and the detailed description of elements related with the present disclosure may make the gist of the present disclosure unclear, a detailed description of those elements will be omitted.

Further, in the following description, a module may mean a functional and structural combination of hardware for performing the technical idea of the present invention and software for driving the hardware. For example, the module may refer to a logical unit of a predetermined code and a hardware resource for the predetermined code to be executed, and it can easily be deduced to the average expert in the field of the present invention that it does not necessarily mean physically linked code or a kind of hardware.

Further, it is understood that each configuration of first to fifth peroral endoscopic apparatuses of a swallowable type 100, 600 to 900, and 900*a* according to various embodiments of the present invention shown in FIGS. 5, 6, 9 to 12A, and 12B is functionally and logically separable, and the average expert in the field of the present invention can easily infer that each configuration does not necessarily mean that it is separated into separate physical devices or written in separate codes.

Hereinbelow, the specific technical contents to be implemented in the present invention will be described in detail with reference to the accompanying drawings.

FIG. 1 is a schematic view showing a peroral endoscope system with a peroral endoscopic apparatus 100 of a swallowable type according to the first embodiment of the present invention applied thereto.

Referring to FIG. 1, the peroral endoscope system according to the embodiment of the present invention may include the peroral endoscopic apparatus 100, a magnetic controller 200, a receiver 300, and a monitoring device 400.

The peroral endoscopic apparatus 100 shown in FIG. 1 may be one of first to fifth peroral endoscopic apparatuses 600 to 900, and 900*a* to be described with reference to FIGS. 9 to 12A, and 12B.

The peroral endoscopic apparatus 100 is a mouth-swallowable capsule, which can perform imaging using an image sensor and perform ultrasonic imaging using an ultrasonic sensor. Further, the peroral endoscopic apparatus 100 according to the embodiment of the present invention is provided with a permanent magnet, and a posture and a proceeding direction of the peroral endoscopic apparatus 100 can be controlled by an external magnetic force generated from the magnetic controller 200. In particular, by the control of the posture, the peroral endoscopic apparatus 100 is brought into close contact with the stomach inner wall by the permanent magnet and the magnetic controller 200 so as to perform imaging of the stomach inner wall or a submucosal region of the inner wall.

The magnetic controller 200 can control a position, a posture, and a proceeding direction of the peroral endoscopic apparatus 100 by using an external magnetic generating an external magnetic force, and in the embodiment of the present invention, the magnetic controller 200 may be of the handheld type that can be hand held by an operator or may be of a type that is mounted to the end of the articulated robot arm and remotely operated automatically semi-automatically. The important point here is that the magnetic controller 200 is of such a small size that it can be manipulated by a hand or a robot arm and is configured to be brought into close contact with or close to a patient's upper body so that a magnetic force can be directly applied to the peroral endoscopic apparatus 100. In this respect, there is a clear difference from a conventional large-sized magnetic device which forms a strong magnetic field around the human body.

The operator brings the magnetic controller 200 close to the abdomen of the patient who swallowed the peroral endoscopic apparatus 100 and can adjust the intensity of the may force suitable for the patient's body condition. The operator puts the magnetic controller 200 on the abdomen of the patient who swallowed the peroral endoscopic apparatus 100 and checks the position of the peroral endoscopic apparatus 100 inside the digestive system through a screen of the monitoring device 400.

Further, when the operator moves the magnetic controller 200 on the abdomen, the may controller 200 is moved, whereby the direction of the magnetic force generated from the external magnetic changes, and thus the posture or proceeding direction of the peroral endoscopic apparatus 100 can be controlled. In other words, the magnetic controller 200 controls the posture and proceeding direction of the peroral endoscopic apparatus 100 according to manual manipulation of the operator (or remote manipulation of the robot arm), whereby the peroral endoscopic apparatus 100 is moved to the inner wall which needs to be imaged in the digestive system, and the submucosal region or the inner wall or the inner wall which needs to be imaged is imaged by the image sensor and/or the ultrasonic sensor and can wirelessly transmit to the receiver 300.

The receiver 300 receives image data or ultrasonic data of each sensor output from the peroral endoscopic apparatus 100 and transmits the same to the monitoring device 400. Further, the receiver 300 receives an operation control signal for controlling the operation of the peroral endoscopic apparatus 100 output from the monitoring device 400 and transmits the same to the peroral endoscopic apparatus 100. The operation control signal includes, for example, a signal for controlling an imaging unit 120 and an ultrasonic unit 130, which will be described hereinafter, to perform imaging simultaneously or sequentially.

The monitoring device 400 may be a personal computer (PC) that analyzes the image data and the ultrasonic data received through the receiver 300, processes the same in a displayable form, and displays the processed data on the screen.

FIG. 2 is a schematic view showing a peroral endoscope system with the peroral endoscopic apparatus 100 of a swallowable type according to the second embodiment of the present invention applied thereto.

The second peroral endoscope system shown in FIG. 2 is similar to the first peroral endoscope system described with reference to FIG. 1.

However, in the case of FIG. 1, the magnetic controller 200 controls the posture and proceeding direction of the peroral endoscopic apparatus 100, and the operation control signal is generated from the monitoring device 400.

On the contrary, a magnetic controller 200a shown in FIG. 2 itself can generate the operation control signal instead of the monitoring device 400 and output the same to the receiver 300. The receiver 300 transmits the operation control signal received from the magnetic controller 200a to the peroral endoscopic apparatus 100.

FIG. 3 is a schematic view showing a peroral endoscope system with the peroral endoscopic apparatus 100 of a swallowable type according to the third embodiment of the present invention applied thereto.

The third peroral endoscope system shown in FIG. 3 is similar to the first peroral endoscope system described above. However, in the case of FIG. 3, a magnetic controller 200b itself can generate the operation control signal for controlling the peroral endoscopic apparatus 100 and transmit the same to the peroral endoscopic apparatus 100 directly. Further, the magnetic controller 200b can transmit the image data or ultrasonic data of each sensor received from the peroral endoscopic apparatus 100 to the receiver 300. In this case, the peroral endoscopic apparatus 100 and the magnetic controller 200b may communicate using a galvanic coupling method described later or using RF communication technology.

FIG. 4 is a schematic view showing a peroral endoscope system with the peroral endoscopic apparatus 100 of a swallowable type according to the fourth embodiment of the present invention applied thereto.

The fourth peroral endoscope system shown in FIG. 4 is similar to the third peroral endoscope system described above. However, in the case of FIG. 4, it is different in that a magnetic controller 200c has the receiver 300 mounted therein. The image data or ultrasonic data received from the peroral endoscopic apparatus 100 may be collected and stored in the receiver 300, and the stored image data or ultrasonic data may be transmitted to the monitoring device 400.

FIG. 5 is a block diagram showing the peroral endoscopic apparatus 100 according to the embodiment of the present invention.

Referring to FIG. 5, the peroral endoscopic apparatus 100 according to the embodiment of the present invention may include a transceiving unit 110, the imaging unit 120, the ultrasonic unit 130, a power supply unit 140, a magnetic unit 150, and a control unit 160.

The transceiving unit 110 receives the operation control signal output from the monitoring device 400 through the receiver 300 or the magnetic controller 200a, 200b, 200c and transmits the same to the control unit 160. Further, the transceiving unit 110 transmits the image data output from the imaging unit 120 or the ultrasonic chat a output from the ultrasonic unit 130 to an external device such as the receiver 300.

The transceiving unit 110 may use the galvanic coupling method or RF communication technology requiring an antenna, and may support one-way wireless communication or two-way wireless communication. The transceiving unit 110 may be constituted by at least one application specific integrated circuit (ASIC).

The galvanic coupling method is a method in which a signal electrode (+) and around electrode (-) of the transceiver are respectively attached to the human body to cause a change in the electric field by a potential difference between the two electrodes, and is advantageous in that there is no need for an antenna for signal transmission and reception, and low power consumption and downsizing are possible.

The at least one imaging unit 120 outputs the image data within the visible light region by imaging the inner wall of the digestive system in real time or intermittently while the peroral endoscopic apparatus 100 is moved through the digestive system of the human body. To achieve this, the imaging unit 120 may include at least one image sensor such as a charge coupled device (CCD) or a complementary metal oxide semiconductor (CMOS), and optical elements for camera imaging such as at least one optical lens and an illumination device such as a light emitting diode (LED). The illumination device can emit light of a predetermined color such as white light and blue light.

The at least one ultrasonic unit 130 may output the ultrasonic image data on a region beneath an inner wall of the digestive system (hereinafter, referred to as 'submucosal region') and a peripheral organ located around the digestive system in real time or intermittently while the peroral endoscopic apparatus 100 is moved through the digestive system of the human body. The peripheral organs of the digestive system include the pancreas, spleen, kidney, liver, gallbladder, salivary gland, heart, lung, large intestine, etc.

For example, since the pancreas, which is one of the peripheral organs of the stomach, is located close to pylorus, pyloric antrum, or greater curvature of the stomach, the imaging unit 120 may detect the abnormality by taking a close-up of a part facing the pancreas of the stomach inner wall, and on the other hand, the ultrasonic unit 130 may perform ultrasonic imaging of the submucosal region of the inner wall facing the pancreas to identify the disease.

In this case, patients can be easily screened for abnormalities of peripheral organs such as the pancreas without a CT scan or an ultrasonic endoscope using a probe for areas, such as the pancreas, which are difficult to be imaged.

According to the embodiment of the present invention, of the peroral endoscopic apparatus 100, the surface facing the at least one ultrasonic unit 130 may be formed to be flat. For example, when the surface facing the at least one ultrasonic unit 130 is a side surface of the peroral endoscopic apparatus 100, the entire side surface 130 may be formed to be flat or a part of the entire side surface (that is, a part of the side surface that directly faces the at least one ultrasonic unit 130) may be formed to be flat.

Further, the at least one ultrasonic unit 130 may be provided to be in close contact with the facing surface, whereby it is possible to perform ultrasonic imaging precisely and clearly. In other words, as the surface of the peroral endoscopic apparatus 100 facing the ultrasonic unit 130 is formed to be flat, the peroral endoscopic apparatus 100 can be brought into close contact the inner wall of the digestive system, whereby the air layer between the ultrasonic unit 130 and the inner wall of the digestive system is eliminated, and thus clear ultrasonic imaging is possible.

The flat surface facing the at least one ultrasonic unit 130 or at least one ultrasonic transducer should include an outer surface of a main body of the peroral endoscopic apparatus 100. For example, only the outer surface may be formed to be flat and the inner surface facing the outer surface may be formed to be curved or both the outer surface and the inner surface facing the outer surface may be formed to be flat. The important point here is that the outer surface brought in direct contact with the inner wall of the digestive system should be flat to eliminate the air layer between the ultrasonic unit 130 and the inner wall of the digestive system, and the inner surface of the peroral endoscopic apparatus 100 in which the ultrasonic unit 130 is provided need not necessarily be flat.

Further, when the ultrasonic unit 130 of the peroral endoscopic apparatus 100 is provided in plural, the plurality of ultrasonic units may be provided on at least one surface of front, rear, and side surfaces of the peroral endoscopic apparatus 100. For example, when the peroral endoscopic apparatus 100 is formed in a cylindrical shape, the surface having circular section is referred to as a front surface, the opposite surface referred to as a rear surface, and the remaining surface corresponding to the column is referred to as a side surface, and the plurality of ultrasonic units may be provided only on the front surface, provided on the front surface and the side surface, provided on the front surface and the rear surface, or provided on the front surface, the rear surface, and the side surface, and may perform ultrasonic imaging at the same time or at different times. This is equally applicable when the peroral endoscopic apparatus 100 is formed in a capsule shape.

FIG. 6 is a block diagram showing the ultrasonic unit 130 according to the embodiment of the present invention.

Referring to FIG. 6, the ultrasonic unit 130 includes multiple high voltage (HV) pulsers 131, an HV Tx/Rx switch 132, an transducer array 133, multiple pre-AMPs 134, multiple variable gain amplifiers (VGAs) 135, multiple low pass filters (LPFs) 136, and multiple analog/digital converters (ADCs) 137.

The number of the multiple HV pulsers 131, the HV Tx/Rx switch 132, the transducer array 133, the multiple pre-AMPs 134, the multiple VGAs 135, the multiple LPFs 136, and the multiple ADCs 137 is the same as the number of the ultrasonic transducers provided in the transducer array 133, and the operation thereof is the same.

When the control unit 160 receives an operation control signal for operating the ultrasonic frequency to be activated from the controllers 200a, 200b, and 200c, the control unit controls the multiple HV pulsers 131 to generate a pulse corresponding to the ultrasonic frequency of the received operation control signal.

The multiple HV pulsers 131 generate pulses to generate the received ultrasonic frequency and transmit the same to the HV Tx/Rx switch 132.

The HV Tx/Rx switch 132 switches the pulse received from each HV pulser 131 to the corresponding ultrasonic transducer of the transducer array.

The transducer array 133 is a multi-transducer array with multiple ultrasonic transducers arrayed. The multiple ultrasonic transducers generate transducery waves by oscillating according to the pulse received through the HV Tx/Rx switch 132. Further, the transducer array 133 may be provided with transducer. This is because the peroral endoscopic apparatus 100 according to the embodiment of the present invention is intended to focus on one-directional imaging rather than omni-directional imaging, and by using one transducer, ultrasonic imaging of the submucosal region is possible. Thus, by performing one-directional imaging in comparison with the omni-directional imaging to minimize errors due to positional changes, more precise ultrasound images can be obtained and more accurate screening can be performed.

The transducery wave scanned along the scanning range to the stomach inner wall is reflected from the inner wall and received by each ultrasonic transducer.

The ultrasonic transducers of the transducer array 133 transmit the reflectively received transducery wave to the HV Tx/Rx switch 132, and the HV Tx/Rx switch 132 switches the reflectively received transducery wave to the pre-AMP 134 mapped to each ultrasonic transducer.

Each pre-AMP 134 amplifies the reflectively received transducery wave, and each VGA 135 variably amplifies the gain of the amplified transducery wave.

Each LPF 136 low-passes the variable-gain amplified transducery wave to remove noise, and each ADC 137 converts the transducery wave from which noise has been removed to a digital signal.

The control unit 160 processes the digital signal input from each ADC 137 using a digital signal processor (DSP) and then controls the transceiving unit 110 to transmit the digital signal to the receiver 300.

Hereinafter, an operation of ultrasonic imaging of the pancreas using the peroral endoscopic apparatus 100 will be described with reference to FIG. 7.

FIG. 7 is a view showing the stomach 510 and the pancreas 540 located around the stomach of human digestive system.

Referring to FIG. 7, the pancreas 540 has a slender, long-shape of about 15 cm, is positioned behind the stomach 510, is connected to a duodenum 530, and is adjacent to the spleen. The pancreas 540 is divided into three parts: head, trunk, and tail. The part near the duodenum 530 is the head, the middle is the body, and the thinnest part is the tail. In general, it is very important to identify the location of a disease, as the disease associated with pancreas 540 may be different depending on which part of the pancreas 540 the disease has developed.

As shown in FIG. 7, since the pancreas 540 is in close contact with the stomach 510 and the duodenum 530, as in the embodiment of the present invention, by using a magnetic force, the peroral endoscopic apparatus 100 is brought in close contact with the stomach 510 inner wall and the duodenum 530 closest to the pancreas 540, and then ultrasonic imaging of the head, trunk and tail of the pancreas 540 can be performed using different or the same frequency suitable for performing imaging of the pancreas 540.

Here, the peroral endoscopic apparatus 100 can perform imaging of the stomach 510 inner wall corresponding to the trunk or tail of the pancreas 540 using the imaging unit 120 at a location near the pyloric antrum or greater curvature of the stomach 510, and perform ultrasonic imaging of the trunk of the pancreas 540 using the ultrasonic unit 130.

Further, when the pylorus 520 where the stomach 510 and the duodenum 530 are connected to each other is relaxed by a drug, the peroral endoscopic apparatus 100 moved to the duodenum 530 by using the external magnetic force of the magnetic controller 200. The peroral endoscopic apparatus 100 can perform imaging again of the inner wall of the duodenum 530 at a location of the duodenum 530 corresponding to the trunk or tail of the pancreas 540 using the imaging unit 120, and perform ultrasonic imaging of the head or tail of the pancreas 540 using the ultrasonic unit 130.

Referring again to FIG. 5, the power supply unit 140 supplies power to each of the components 110 to 160 of the peroral endoscopic apparatus 100. The power supply unit 140 may include a rechargeable battery or a non-rechargeable replaceable battery. The charging method of the rechargeable battery may be selectively applied with one of multiple wireless power charging methods including a magnetic induction method, a magnetic resonance method, or an electromagnetic wave method. Further, the power supply unit 140 enables on/off of the power supply.

The magnetic unit 150 is a component that can control the posture and proceeding direction of the peroral endoscopic apparatus 100 in response to the external magnetic force, and may include at least one permanent magnet. In other words, the magnetic unit 150 may be configured to control posture adjustment and proceeding directions of the peroral endoscopic apparatus 100 for positional movement, rotation thereof, and imaging by using the magnetic force generated from the magnetic controller 200.

In particular, the magnetic unit 150 may allow peroral endoscopic apparatus 100 to be brought in close contact with the inner wall the digestive system by interaction with the external magnetic force.

When the magnetic unit 150 includes at least two permanent magnets, the power supply unit 140 of a battery type may be disposed between the at least two permanent magnets. This is because the magnetic unit 150 and the power supply unit 140 are the heaviest components of the peroral endoscopic apparatus 100, and placing the power supply unit 140 at the center with the permanent magnets on opposite sides thereof is advantageous for balancing the overall weight of the peroral endoscopic apparatus 100. If the weight balance of the peroral endoscopic apparatus 100 is highly unbalanced, the magnetic controller 200 has difficulty in controlling posture and proceeding direction of the peroral endoscopic apparatus. Further, if the distance between at least two permanent magnets is as large as possible, when the peroral endoscopic apparatus 100 is brought in close contact with the inner wall of the digestive system by using the external magnetic force of the magnetic controller 200, is also advantageous in terms of ultrasonic imaging because can suppress the occurrence of air due to lift-off.

FIG. 8 is a conceptual view showing an example of arrangement of two permanent magnets 152 and 154 and the power supply unit 140. Referring to FIG. 8, the magnetic unit 150 includes two permanent magnets 152 and 154, and the conductive power supply unit 200 is provided between the two permanent magnets 152 and 154. When the permanent magnets 152 and 154 are arranged to have a N/S pole and a N/S pole, respectively, the magnetic unit 150 can be a shape having a large N/S pole and can form a larger magnetic force.

The control unit 160 controls the overall operation of the peroral endoscopic apparatus 100. When receiving the operation control signal output from the monitoring device 400 or the magnetic controller 200a, 200b, 200c through the transceiving unit 110, the control unit 160 can control to perform an operation corresponding to the operation control signal.

For example, when an operation control signal for causing the imaging unit 120 and the ultrasonic unit 130 to simultaneously perform imaging of the inner wall is received, the control unit 160 controls the imaging unit 120 and the ultrasonic unit 130 to simultaneously or individually perform imaging of the submucosal regions of the inner wall or the inner wall that the imaging unit 120 and the ultrasonic unit 130 face at the moment.

Further, when the magnetic controller 200 controls the posture and proceeding direction of the magnetic unit 150 such that the peroral endoscopic apparatus 100 is moved to the stomach inner wall closest to a peripheral organ of the digestive system, the magnetic unit 150 responds to this and the peroral endoscopic apparatus 100 is moved to the stomach inner wall closest to the peripheral organ. In this case, the control unit 160 may control the imaging unit 120 such that the peroral endoscopic apparatus 100 performs imaging of the stomach inner wall closest to the peripheral organ. When the operator monitoring the monitoring device 400 finds an abnormality in the currently imaged inner wall or commands ultrasonic imaging even though it is not detected, the control unit 160 may control the ultrasonic unit 130 to perform imaging of the submucosal region of the current inner wall.

Further, if the peripheral organ for close-up imaging is the pancreas, the operator may adjust the frequency to perform imaging of the head, tail, and center of the pancreas. Accordingly, by the operation control signal received from the monitoring device 400 or the magnetic controller 200a, 200b, 200c, the control unit 160 may control the ultrasonic unit 130 to perform imaging of the pancreas by differentiating a frequency of performing imaging of a central part of the pancreas and a frequency of performing imaging of head and tail parts of the pancreas. This is due to the fact that as the ultrasonic frequency increases, the resolution increases while the frequency scanning depth (or the visible range) becomes shorter, and as the ultrasonic frequency decreases, the resolution becomes lower while the frequency scanning depth becomes deeper.

Further, when the image data from the imaging unit 120 and the ultrasonic data from the ultrasonic unit 130 are received, the control unit 160 controls the transceiving unit 110 to transmit the received image data and ultrasonic data in a frame format to the receiver 300.

Further, the control unit 160 may control the power supply unit 140 to simultaneously or selectively turn on/off the power supplied to the imaging unit 120 or the ultrasonic unit 130 according to the operation control signal.

Further, the control unit 160 may control the power supply unit 140 such that the power supply unit 140 is powered on or off according to the operation control signal.

Further, the control unit 160 may control the resolution of the imaging unit 120 or the ultrasonic unit 130, that is, the frames per second (FPS) in the range of 2 to N.

Further, the control unit 160 may transmit an automatic gain control (AGC) command of the imaging unit 120 and transmit ultrasonic frequency, voltage, and amplifier control commands to the ultrasonic unit 130.

Hereinafter, the peroral endoscopic apparatus 100 according to various embodiments of the present invention will be described with reference to FIGS. 9 to 12A and 12B.

The peroral endoscopic apparatus 100 described with reference to FIGS. 1 to 7 may be one of the first to fifth peroral endoscopic apparatuses 600 to 900, and 900a to be described with reference to FIGS. 9 to 12A, and 12B. Thus, the first to fifth peroral endoscopic apparatuses 600 to 900, and 900a shown in FIGS. 9 to 12A, and 12B include the compartments described with reference to FIG. 5, and a detailed description of the same portions is omitted for convenience of explanation.

Further, first to fifth imaging units, first to fifth ultrasonic units, first to fifth image sensors 610 to 910, and 910*a*, first to fifth ultrasonic transducers 620 to 920, and 920*a* described with reference to FIGS. 9 to 12A and 12B may be the imaging unit 120, the ultrasonic unit 130, a sensor such as CMOS of the imaging unit 120, and the ultrasonic transducers provided in the transducer array 133 described with reference to FIGS. 5 and 8.

Further, a part of each of main bodies 630 to 930 and 930*a* of the first to fifth peroral endoscopic apparatus apparatuses 600 to 900, and 900*a* shown in FIGS. 9 to 12A, and 12B is made of materials capable of detecting ultrasonic waves.

Firstly, FIG. 9 is a conceptual view schematically showing a first peroral endoscopic apparatus 600 according to the first embodiment of the present invention.

Referring to FIG. 9, the first peroral endoscopic apparatus 600 includes a first image sensor 610 of a first imaging unit and first ultrasonic transducers 620 of a first ultrasonic unit arranged in parallel with each other along a same line of the peroral endoscopic apparatus 600 to perform imaging toward a same direction, that is, perform imaging of the inner wall at the same position in the digestive system. In other words, the first image sensor 610 and the multiple first ultrasonic transducers 620 are arranged in line along the same line of the first peroral endoscopic apparatus 600.

Here, the first image sensor 610 may be provided next to the outermost transducer of the first ultrasonic transducers 620.

Further, FIG. 9 is an example showing an arrangement relationship of the multiple first ultrasonic transducers 620 included in one first ultrasonic unit, or an example showing an arrangement relationship of the multiple first ultrasonic units when one first ultrasonic unit includes one first ultrasonic transducer 620. This is also applied to the embodiments shown in FIGS. 10 to 11.

FIG. 10 is a conceptual view schematically showing a second peroral endoscopic apparatus 700 according to the second embodiment of the present invention.

The second peroral endoscopic apparatus 700 shown in FIG. 10 is almost identical to the first peroral endoscopic apparatus 600 described with reference to FIG. 9. However, a second image sensor 710 of the second peroral endoscopic apparatus 700 may be provided between second ultrasonic transducers 720 such that the angle of view of the second image sensor 710 and the ultrasonic scanning range of the second ultrasonic transducers 720 overlap as much as possible.

FIG. 11 is a conceptual view schematically showing a third peroral endoscopic apparatus 800 according to the third embodiment of the present invention.

The third peroral endoscopic apparatus 800 shown in FIG. 11 is almost identical to the first peroral endoscopic apparatus 600 described with reference to FIG. 9. However, of the third peroral endoscopic apparatus 800, a surface provided with third ultrasonic transducers 820, that is, a surface on which the ultrasonic waves are reflected against the ultrasonic transducers 820 may be formed into a curved surface having a curvature C greater than zero. In order for the ultrasonic waves scanned from the third ultrasonic transducers 820 not to pass through the air layer, it is best that the surface provided with the third ultrasonic transducers 820 is flat, but there may be cases where it is necessary to form a curved surface on the outer surface of the third peroral endoscopic apparatus 800 due to some design factors. Also, in this case, in order for the third peroral endoscopic apparatus 800 to be brought in close contact with the inner wall of the digestive system as much as possible, it is preferred that curved surface should have a positive curvature and the curvature value thereof should be as small as possible.

FIG. 12A is a conceptual view schematically showing a fourth peroral endoscopic apparatus 900 according to the fourth embodiment of the present invention.

Referring to FIG. 12A, the fourth peroral endoscopic apparatus 900 is configured such that a fourth image sensor 910 and fourth ultrasonic transducers 920 are arranged in parallel with each other to perform imaging toward a same direction, that is, perform imaging of the inner wall at the same position in the digestive system.

In particular, the fourth image sensor 910 and the fourth ultrasonic transducers 920 may be arranged in two rows in parallel with each other along the inner surface corresponding to the circumference of the cylindrical fourth peroral endoscopic apparatus 900.

The fourth image sensor 910, as shown in FIG. 12A, may be provided to be spaced by a predetermined distance from the inner surface of a case of the fourth peroral endoscopic apparatus 900, or may be provided to be in close contact with the inner surface of the case of the fourth peroral endoscopic apparatus 900, which is not shown. Herein, the shape or size of the fourth image sensor 910 is not limited.

Further, the fourth ultrasonic transducers 920 may be arranged along at least one arc that is a part of the circumference of the peroral endoscopic apparatus 900.

Further, although not shown in FIG. 12A, the fourth image sensor 910 and the fourth ultrasonic transducers 920 may be provided along the entire circumference.

FIG. 12B is a conceptual view schematically showing a fifth peroral endoscopic apparatus 900*a* according to the fifth embodiment of the present.

Referring to FIG. 12B, the fifth peroral endoscopic apparatus 900*a* may have a cylindrical shape and a fifth image sensor 910*a* and fifth ultrasonic transducers 920*a* may be arranged along the same line on either the front surface or the rear surface of the fifth peroral endoscopic apparatus 900*a*.

In the case of the fifth peroral endoscopic apparatus 900*a* shown in FIG. 12B, a surface provided with the fifth ultrasonic transducers 920*a*, that is, a surface facing the fifth ultrasonic transducers 920*a* is formed to be flat, and the fifth ultrasonic transducers 920*a* may be provided to be in close contact with the flat surface.

In FIGS. 9 to 12B, multiple first to fifth ultrasonic transducers are provided respectively, but one first to fifth ultrasonic transducer may be provided.

Further, in the first to third peroral endoscopic apparatuses 600, 700, and 800 and the fifth peroral endoscopic apparatus 900*a* described with reference to FIGS. 9, 10, 11, and 12B, when the ultrasonic sensor is applied to the side surface or front surface of each main body 630, 730, 830, 930*a*, the side surface or the front surface is formed to be flat, such that the side surface or the front surface of each of the first to third peroral endoscopic apparatuses 600, 700, and 800 and the fifth peroral endoscopic apparatus 900*a* is brought in close contact with the inner wall of the digestive system.

FIG. 13 is a flow chart showing how to perform endoscopy of a pancreas with the peroral endoscopic apparatus 100 according to the embodiment of the present invention.

Referring to FIG. 13, when the peroral endoscopic apparatus 100 enters the patient's digestive system, the operator controls movement of the peroral endoscopic apparatus 100 using the magnetic controller 200 placed on the patient's abdomen (S1010).

By the operation control signal of the monitoring device 400 or the magnetic controller 200a, 200b, 200c, the peroral endoscopic apparatus 100 activates the imaging unit 120 to start performing imaging of the digestive system (S1020).

The peroral endoscopic apparatus 100 is moved to the stomach inner wall closest to the pancreas by the external magnetic force of the magnetic controller 200 (S1030). In other words, the operator determines the position close to the pancreas while observing the image imaged by the imaging unit 120 and displayed on the monitoring device 400, and manipulates the magnetic controller 200 to move the peroral endoscopic apparatus 100.

At the stomach inner wall close to the pancreas, the peroral endoscopic apparatus 100 turns off the operation of the imaging unit 120 and turns on the ultrasonic unit 130 by the operation control signal if necessary (S1040).

Further, the peroral endoscopic apparatus 100 is brought in contact with the stomach inner wall as close as possible by the external magnetic force of the magnetic controller 200, 200a, 200b or 200c, and then controls the ultrasonic unit 130 generate a corresponding frequency according to the ultrasonic frequency defined by the monitoring device 400 or the magnetic controller 200a, 200b, 200c (S1050).

The ultrasonic unit 130 of the peroral endoscopic apparatus 100 generates a transducery wave corresponding to the ultrasonic frequency, receives the transducery wave reflected from the inner wall, processes the signal by gain amplification and digital conversion, and outputs ultrasonic data (S1060). Thereby, ultrasonic data corresponding to a part of the pancreas is output.

The peroral endoscopic apparatus 100 transmits the ultrasonic data output in the step S1060 to the receiver 300 (S1070).

By the step S1070, ultrasonic imaging of a part of the pancreas is completed, and whether the pylorus of the stomach is relaxed by the drug or the like injected before the step S1010 is checked.

Once the pylorus has been found to be relaxed to such an extent that the peroral endoscopic apparatus 100 can be moved, the peroral endoscopic apparatus 100 is guided by the external magnetic force of the magnetic controller 200, passes through the pylorus of the stomach, and is moved to the duodenum adjacent to the head of the pancreas (S1080). In the step S1070 or after the step S1070, the ultrasonic unit 130 is turned off and the imaging unit 120 is turned on, the illumination device of the imaging unit 120 can emit light.

Again, at the inner wall of the duodenum adjacent to the head of the pancreas, the peroral endoscopic apparatus 100 turns on the ultrasonic unit 130 by the operation control signal (S1090). In step S1040 and step S1090, the imaging unit 120 may be kept on or off, which may be selectively applied in consideration of the ambient conditions. Ambient conditions may include, for example, battery level, and inner/outer wall conditions of the stomach, the pancreas or the duodenum.

Further, the peroral endoscopic apparatus 100 is brought close contact with the inner wall of the duodenum by the external magnetic force of the magnetic controller 200, 200a, 200b or 200c, and then controls the ultrasonic unit 130 to generate a corresponding frequency according to the ultrasonic frequency defined by the monitoring device 400 or the magnetic controller 200a, 200b, 200c (S1100).

The ultrasonic unit 130 of the peroral endoscopic apparatus 100 performs imaging of the pancreas with the transducery wave corresponding to the ultrasonic frequency and outputs the ultrasonic data (S1110).

The peroral endoscopic apparatus 100 transmits the ultrasonic data output in the step S1110 to the receiver 300 (S1120).

The monitoring device 400 analyzes and processes the image data and the ultrasonic data received through the receiver 300 as a displayable signal, and displays the processed data on the screen.

Meanwhile, it is easily understood by those skilled in the art that the endoscopic method for a pancreas with the peroral endoscopic apparatus 100 according to the present invention may be provided in a recording medium that is readable through a computer by tangibly embodying a program of instructions for implementing the endoscopic method.

In other words, the endoscopic method with the peroral endoscopic apparatus 100 according to the present invention for a pancreas may be embodied in a form of a program that can be executed through various computer means and be recorded on a computer readable recording medium, and the computer readable recording medium may include program instructions, data files, data structures, etc., alone or in combination thereof. The computer readable recording medium includes magnetic media such as hard disks, optical media such as CD-ROMs and DVDs, and a hardware device specifically configured to store and execute program instructions, such as ROM, RAM, flash memory, USB memory, and the like.

Accordingly, the present invention also provides 1 program stored on a computer readable recording medium that is executed on a computer for controlling the electromagnetic characteristic measurement system as to implement the endoscopic method with the peroral endoscopic apparatus 100 for the pancreas.

INDUSTRIAL APPLICABILITY

The present invention is useful for use as a peroral endoscopic apparatus capable of monitoring the digestive system and surrounding organs by using an ultrasonic wave.

The invention claimed is:

1. A peroral endoscopic apparatus of a swallowable type, the peroral endoscopic apparatus comprising:
    at least one imaging unit configured to perform imaging of a human body digestive system while moving in the digestive system and output image data;
    at least one ultrasonic unit configured to output ultrasonic data on a region beneath an inner wall of the digestive system (hereinafter, referred to as 'submucosal region') and a peripheral organ located around the digestive system;
    a magnetic unit configured to adjust a position, a posture, and a proceeding direction of the peroral endoscopic apparatus in response to an external magnetic force;
    a transceiving unit configured to transmit the image data and the ultrasonic data to an external device or receive an external control signal;
    a control unit configured to control the at least one imaging unit and the at least one ultrasonic unit to perform imaging of the digestive system and the submucosal region simultaneously or individually; and
    a power supply unit configured to supply power to the at least one imaging unit, the at least one ultrasonic unit, the magnetic unit, the transceiving unit, and the control unit,
    wherein the at least one ultrasonic unit is provided so as to be in close contact with an opposing surface of the peroral endoscopic apparatus, wherein the magnetic unit allows the peroral endoscopic apparatus to be brought in close contact with the inner wall of the digestive system by interaction with the external magnetic force, wherein of the peroral endoscopic apparatus, a surface facing the at least one ultrasonic unit is formed to be flat, wherein of a main body of the peroral endoscopic apparatus, a surface facing the at least one ultrasonic transducer of the at least one ultrasonic unit is formed to be flat, such that the at least one ultrasonic transducer is provided to be in close contact with the flat surface, wherein an image sensor of the at least one imaging unit and at least one ultrasonic transducer of the at least one ultrasonic unit are arranged in parallel with each other along a same line of the peroral endoscopic apparatus to perform imaging toward a same direction in the digestive system, and wherein when the ultrasonic transducer is provided in plural, the image sensor of the at least one imaging unit is provided between the ultrasonic transducers such that an angle of view of the image sensor and an ultrasonic scanning range of the ultrasonic transducers are overlapped with each other.

2. The peroral endoscopic apparatus of claim 1, wherein the external magnetic force is generated by an external magnetic controller to drive the magnetic unit, and the magnetic controller is configured to be brought in close contact with or close to a patient's upper body to allow the external magnetic force to act on the magnetic unit.

3. The peroral endoscopic apparatus of claim 2, wherein the magnetic controller controls the magnetic unit such that the peroral endoscopic apparatus is moved to a stomach inner wall closest to the peripheral organ; and the control unit controls the at least one imaging unit to perform imaging of the closest stomach inner wall when the peroral endoscopic apparatus is moved to the stomach inner wall closest to the peripheral organ, and controls the at least one ultrasonic unit to perform imaging of a submucosal region of the closest stomach.

4. The peroral endoscopic apparatus of claim 1, wherein when the peripheral organ is a pancreas, the control unit controls the at least one ultrasonic unit to perform imaging of the pancreas by differentiating a frequency of performing imaging of a central part of the pancreas and a frequency of performing imaging of head and tail parts of the pancreas.

5. The peroral endoscopic apparatus of claim 1, wherein of the peroral endoscopic apparatus, a surface facing the at least one ultrasonic transducer is formed as a curved surface having a positive curvature.

6. The peroral endoscopic apparatus of claim 1, wherein an image sensor of the at least one imaging unit and at least one ultrasonic transducer of the at least one ultrasonic unit are arranged in two rows in parallel with each other along a circumference of the peroral endoscopic apparatus to perform imaging toward a same direction in the digestive system.

7. The peroral endoscopic apparatus of claim 6, wherein the at least one ultrasonic transducer of the at least one ultrasonic unit is arranged along at least one arc that is a part of the circumference of the peroral endoscopic apparatus.

8. The peroral endoscopic apparatus of claim 1, wherein the power supply unit includes at least one of a rechargeable battery and a regular battery other than the rechargeable battery.

9. The peroral endoscopic apparatus of claim 1, wherein the at least one ultrasonic unit is provided to be in close contact with a surface of the peroral endoscopic apparatus facing the at least one ultrasonic unit.

10. The peroral endoscopic apparatus of claim 1, wherein when the ultrasonic unit is provided in plural, the plurality of ultrasonic units are provided on at least one surface of front, rear, and side surfaces of the peroral endoscopic apparatus.

11. The peroral endoscopic apparatus of claim 1, wherein the magnetic unit includes:

a first permanent magnet; and a second permanent magnet, wherein the power supply unit as a conductor is provided between the first permanent magnet and the second permanent magnet.

12. The peroral endoscopic apparatus of claim 11, wherein the magnetic unit allows the peroral endoscopic apparatus to be in close contact with the inner wall of the digestive system by interaction with the external magnetic force.

* * * * *